United States Patent [19]

Linkow et al.

[11] 4,024,638

[45] May 24, 1977

[54] WIDE VENT DENTAL IMPLANTS

[76] Inventors: Leonard I. Linkow, 30 Central Park South, New York, N.Y. 10019; Alfred E. Edelman, 2723 Federal St., Camden, N.J. 08105

[22] Filed: Feb. 24, 1969

[21] Appl. No.: 804,738

Related U.S. Application Data

[63] Continuation-in-part of Ser. No. 480,367, Aug. 17, 1965, Pat. No. 3,479,222.

[52] U.S. Cl. .............................................. 32/10 A
[51] Int. Cl.² ........................................ A61C 13/00
[58] Field of Search .................................. 32/10 A

[56] References Cited
UNITED STATES PATENTS 3,465,441  9/1969  Linkow .............................. 32/10 A
3,729,825  5/1973  Linkow .............................. 32/10 A

OTHER PUBLICATIONS

Implant Research Corp., "The Blade Vent", Box 123, Pennsauken, N.J. 08110, copyright 1968.

*Primary Examiner*—Robert Peshock

[57] ABSTRACT

A wide vent dental implant adapted to be driven into the jaw bone of an individual and having a wide flat blade portion offering a large surface area for frictional retention in the jaw bone, and a head portion which remains exposed outside the jaw and provides a support for dental appliances of various types requiring an anchorage to the jaw bone. The bottom edge of the blade portion is sharpened to provide a cutting edge which incises the jaw bone as the wide vent is driven into place.

8 Claims, 11 Drawing Figures

U.S. Patent
May 24, 1977
4,024,638
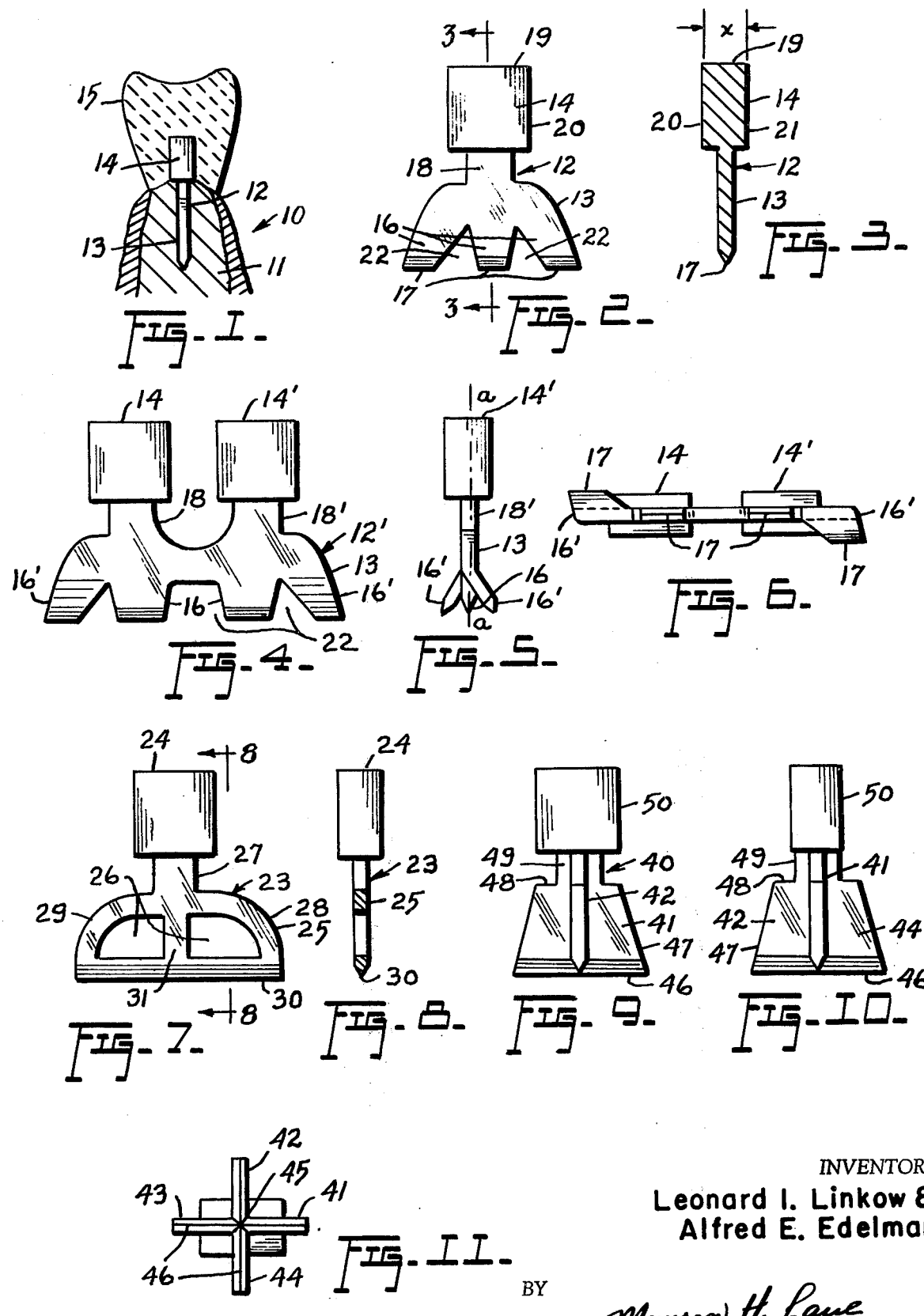
INVENTORS
Leonard I. Linkow &
Alfred E. Edelman
BY Munson H. Lane
ATTORNEY

WIDE VENT DENTAL IMPLANTS

The present application is a continuation-in-part of our earlier application Ser. No. 480,367, filed Aug. 17, 1965, now Pat. No. 3,479,222, dated Mar. 10, 1970. This invention relates to dental implants and specifically to wide vent implants which are adapted to be driven into the jaw bone of a patient by impact or pressure driving means.

Heretofore, implants of the endosseous type (internal in bone) have been made by removing some of the bone area to form a socket and then replacing that area with a metallic or plastic substance of generally circular cross sectional configuration. In many of the implants made according to the prior art the bone which is removed in forming the socket in the jaw is discarded with a resultant bone loss to the patient which could be significant in many cases as a cause of failure of the implant. In some cases the implant has a hollow core and the bone removed in forming the socket can be replaced within the hollow core of the implant. Present causes of failure of implants are attributed to bone loss which plays a contributing role as well as the fact that lateral stresses are not adequately compensated for when the implant has a circular configuration.

The implant of this invention is characterized by a flat, thin blade design which makes it unnecessary to remove any bone of the cancellous type. Further it offers greater resistance to lateral stresses than the implants of circular design afford.

It is an object of this invention to provide a dental implant which forms its own socket as it is driven into the jaw bone.

It is another object of this invention to provide dental implants having a blade portion with large retention surface areas and with a sharpened bottom edge which cuts its way when forced into the jaw bone, and a head portion which projects from the jaw bone after the blade portion is driven into the jaw bone and to which various dental appliances such as dentures, teeth and orthodontic devices can be secured.

It is a further object of this invention to provide an implant that can be used to circumvent the sinus as a one unit implant. Heretofore, dental implants have not been designed with the aforesaid capability.

It is a further object of this invention to provide an improved dental implant which is satisfactory for use as a one tooth implant and does not require support by an approximating tooth or teeth.

These and other objects, advantages and novel features will be apparent from the following description and the accompanying drawings.

In the drawings:

FIG. 1 is a transverse vertical cross sectional view through a human jaw showing one embodiment of the vent blade of this invention implanted in the jaw bone with a tooth attached thereto.

FIG. 2 is a front elevational view of one embodiment of the invention.

FIG. 3 is a vertical sectional view taken on line 3—3 of FIG. 2.

FIG. 4 is a front elevational view of a second embodiment of the invention.

FIG. 5 is an end elevational view of the embodiment shown in FIG. 4.

FIG. 6 is a bottom plan view of the embodiment shown in FIG. 4.

FIG. 7 is a front elevational view of a third embodiment of the invention.

FIG. 8 is a vertical sectional view taken on line 8—8 of FIG. 7.

FIG. 9 is a front elevational view of a fourth embodiment of the invention.

FIG. 10 is a right side elevational view of the embodiment shown in FIG. 9.

FIG. 11 is a bottom plan view of the embodiment shown in FIGS. 9 and 10.

The drawings are not to scale and show the several modifications of the invention enlarged several times over their actual size for clarity.

Referring to FIG. 1 a human jaw 10 is shown in vertical cross section having a wide vent 12 implanted in the jaw bone 11 and a tooth 15 secured to the head 14 of the wide vent. As seen in FIG. 2 the wide vent includes a wide, flat, thin blade portion 13 having separated tooth portions 16 formed by serrations in the bottom edge of the blade. The tooth portions 16 have sharpened bottom edges 17 formed by beveling the opposite sides of the tooth portions toward the edges 17. A head portion 14, integrally connected to the blade portion 13 by a narrow neck 18, provides means to which dental appliances can be secured. The head portion 14 is shown as being of polygonal shape having wide front and back sides 20 and 21 and a narrow transverse dimention X with a flat top surface 19. While the head 14 is shown as being of polygonal shape with parallel sides and ends it can have other shapes and fall within the scope of this invention.

When the wide vent is to be inserted in the jaw bone it is placed on the ridge of the jaw in vertical alignment with the jaw bone and driven into the bone by hammer blows or by continuous pressure applied to the head portion of the wide vent. The sharpened bottom edges 17 of the wide vent cut their way into the jaw bone and provide a tight fitting opening for the blade portion 12 of the wide vent. Driving pressure applied to the head 14 of the wide vent is discontinued after the blade portion 12 has be fully driven into the jaw bone and only the head portion 14 remains exposed above the jaw. The jaw bone acting on the wide blade 12 offers resistance to lateral stresses which may be applied to the head portion 14 and the design of the blade with serrations 22 in the bottom edge affords a vent opening so that bone can anchor around and through the implant because of the springy texture of the cancellous bone. This is effected immediately on insertion.

A second embodiment of the invention is shown in FIGS. 4, 5 and 6. The second embodiment 12' includes multiple head portions 14 and 14' and a blade portion 13 which is wider than the blade portion of the single headed embodiment of FIGS. 1, 2 and 3 so as to accommodate the multiple heads and at the same time offer a greater surface area to resist the increased total lateral forces which are applied to the multiple heads. The bottom edge of the blade 13 has three serrations forming four separate teeth. The two intermediate teeth 16 are linear continuations of the blade body 13. The two end teeth 16' are curved laterally from a central plane 9—9 through the body of the blade vent, each end tooth extending on an opposite side of the central plane with respect to the other. The laterally curved end teeth 16' provide a greater resistance to upward pulling forces once the wide vent is implanted in the jaw bone than do the straight intermediate teeth 16. The multi-headed wide vent 12' is implanted in the jaw bone by a driving force applied to the heads 14, 14' in the same manner as described with respect to the single headed wide vent 12. The bottom edges 17 of the teeth 16 and 16' are sharpened so that they cut their way into the jaw bone as they are driven.

A third embodiment 23 of the wide vent is shown in FIGS. 7 and 8. The wide vent 23 includes a polygonal head 24 (like the head 14 of the wide vent 12 of FIGS. 1 and 2) and a blade portion 25 connected to the head 24 by a narrow neck 27. The blade portion 25 is a thin, flat blade outlined by downwardly directed curved end margins 28 and 29 extending from the lower portion of the narrow neck 27 to a sharpened straight bottom edge 30. Symmetrical cutout openings 26 are provided on opposite sides of a central body member 31 of the blade portions. The openings 26 provide vent openings so that the cancellous jaw bone can expand through the openings and firmly anchor the wide vent 23 in the bone. Like the first and second embodiments the wide vent 23 is adapted to be driven into the jaw bone.

A fourth embodiment 40 as shown in FIGS. 9, 10 and 11 includes four flat fins 41, 42, 43 and 44 arranged symmetrically about a common axis. The fins are rigidly joined at the common axis 45 and are each perpendicular to an adjacent pair of fins. Each fin has a sharpened bottom edge 46 formed by beveling opposite sides of the fin adjacent the bottom edge. The free outer side edges 47 of the fins slope outwardly and downwardly toward the bottom edges 46 from horizontal shoulders 48 which connect with narrow neck portions 49 that extend upwardly to engage a head portion 50.

As with the other embodiments previously described the four fin vent 40 is adapted to be driven into the jaw bone. However it is usually advantageous to provide a cruciform shaped starting groove in the jaw at the location where the vent 40 is to be implanted. The vent is positioned in the starting groove and then driven into the bone until only the head 50 remains exposed outside the jaw bone. After implanting the vent 40 various dental appliances may be attached to the head 50, in the same manner as they may be connected to the head portions of the other embodiments of the invention as particularly illustrated in FIG. 1 with respect to the embodiment of FIGS. 2 and 3.

Once the vent 40 is implanted by driving it into the bone the cancellous bone is immediately in position to retain the large surface area afforded by the four fins 41, 42, 43 and 44. The four fin blade configuration increases retentive area substantially over the retentive area of an implant of a circular configuration such as has been used in the prior art and which requires that bone be removed in order to form a socket for the implant.

In summary the wide vents of this invention all have in common, a head portion which remains exposed outside of the jaw and which affords means by which dental appliances such as teeth, dentures, and the like may be secured. The vents of this invention also have blade portions with large surface areas which afford a greater retention than do implants of known types which require a preformed socket for the implant. The bottom edges of the blade portions of all embodiments are sharpened so that the blades can be driven into the bone to form their own socket and do not require that a socket be preformed in the jaw to receive the implant.

The vents and entire implant of this invention are preferably made of a strong, corrosion resistant metal such as titanium or alloy, stainless steel or alloy, metal coated with alumina oxide coatings, or other plastic or mineral types of coatings. They may also be fashioned of ceramic type materials which would withstand impact.

Other modifications and variations of the present invention are possible in the light of the above teachings. Accordingly, it is not desired to limit the invention to the present disclosure, and various modifications and equivalents may be resorted to falling within the spirit and scope of the invention as claimed.

What is claimed is:

1. A dental implant comprising at least one head portion, and at least one flat, thin blade portion connected to the head portion by a reduced neck portion, said blade portion having a sharpened bottom edge adapted to incise the jaw bone as the implant is driven into the bone by pressure applied to the head portion. said bottom edge being serrated.

2. A dental implant comprising at least one head portion, and at least one flat, thin blade portion connected to the head portion by a reduced neck portion, said blade portion having a sharpened bottom edge adapted to incise the jaw bone as the implant is driven into the bone by pressure applied to the head portion, said blade portion being substantially wider than it is long. said blade portion being symmetrical about a median line and having curved side margins extending outwardly and downwardly from said reduced neck to said bottom edge.

3. A dental implant comprising at least one head portion, and at least one flat, thin blade portion connected to the head portion by a reduced neck portion, said blade poriton having a sharpened bottom edge adapted to incise the jaw bone as the implant is driven into the bone by pressure applied to the head portion. Said blade portion being symmetrical about a median line and has curved side margins extending outwardly and downwardly from said reduced neck to said bottom edge, and there being a pair of appertures symmetrically arranged on opposite sides of said median line and extending through said blade portion, said bottom edge being straight and uninterrupted throughout its length.

4. A dental implant comprising at least one head portion, and at least one flat, thin blade portion connected to the head portion by a reduced neck portion, said blade portion having a sharpened bottom edge adapted to incise the jaw bone as the implant is driven into the bone by pressure applied to the head portion. Said implant having two head portions each connected to a single flat, thin blade portion by a pair of narrow neck portions.

5. The dental implant set forth in claim 4 wherein said blade portion is substantially wider from side edge to side edge than it is long from the bottom of its neck portion to said sharpened bottom edge.

6. The dental implant set forth in claim 5 wherein said bottom edge is serrated to form at least one intermediate tooth and a pair of end teeth which are curved laterally on opposite sides of said blade portion with respect to each other.

7. A dental impant comprising at least one head portion, and at least one flat, thin blade portion connected to the head portion by a reduced neck portion, said blade portion having a sharpened bottom edge adapted to incise the jaw bone as the implant is driven into the bone by pressure applied to the head portion, said implant having a single head portion and four, thin, flat, blade portions connected to said head portion by a narrow neck, said four blade portions being spaced in series ninety degrees apart about a common line of intersection at which said blades are rigidly connected.

8. The dental implant set forth in claim 7 wherein said blade portions each have downwardly and outwardly sloping straight side edges.

* * * * *